United States Patent
Chen

(10) Patent No.: US 8,772,496 B2
(45) Date of Patent: Jul. 8, 2014

(54) INTERMEDIATE AND PROCESS USEFUL IN THE PREPARATION OF {2-[1-(3,5-BIS-TRIFLUOROMETHYL-BENZYL)-5-PYRIDIN-4-YL-1H-[1,2,3]TRIAZOL-4-YL]-PYRIDIN-3-YL}-(2-CHLOROPHENYL)-METHANONE

(75) Inventor: Pingyun Chen, Chapel Hill, NC (US)

(73) Assignee: Eli Lilly and Company, Indianapolis, IN (US)

( * ) Notice: Subject to any disclaimer, the term of this patent is extended or adjusted under 35 U.S.C. 154(b) by 266 days.

(21) Appl. No.: 12/515,794

(22) PCT Filed: Dec. 4, 2007

(86) PCT No.: PCT/US2007/086319
§ 371 (c)(1),
(2), (4) Date: May 21, 2009

(87) PCT Pub. No.: WO2008/079600
PCT Pub. Date: Jul. 3, 2008

(65) Prior Publication Data
US 2010/0056795 A1    Mar. 4, 2010

Related U.S. Application Data

(60) Provisional application No. 60/870,851, filed on Dec. 20, 2006.

(51) Int. Cl.
    *C07D 401/14*      (2006.01)
(52) U.S. Cl.
    USPC ........................................................ 546/256
(58) Field of Classification Search
    CPC .................................................... C07D 401/14
    USPC ........................................ 546/256; 514/333
    See application file for complete search history.

(56) References Cited

FOREIGN PATENT DOCUMENTS

WO    WO 2005/042515 A    5/2005

OTHER PUBLICATIONS

Seddon, "Psuedopolymorph . . . " Crystal Growth and Design, v. 4(6)1087, 2004 (two pages from internet).*

Bryn et al. "Solid State Chemistry of Drugs" p. 513 (1999).*
Patent Cooperation Treaty, International Preliminary Report on Patentability and Written Opinion of the International Searching Authority for PCT Application No. PCT/US2007/086319 dated Jun. 23, 2009, 6 pages.
Canadian Patent Office, Office Action for CA Application No. 2,671,770 dated Mar. 28, 2012, 2 pages.
Japanese Patent Office, English Translation of Japanese Office Action for JP Application No. 2009-543027 dated Nov. 27, 2012, 4 Pages.
Asahara, "Yozai Handbook," 1985, 3 pages, Kodansha Ltd. (see English translation of JP Office Action for description or article).

* cited by examiner

*Primary Examiner* — Patricia L Morris
(74) *Attorney, Agent, or Firm* — Jayme M. Torelli; Hoffman Warnick LLC

(57) ABSTRACT

The present invention relates to novel compounds, (2-chlorophenyl)-[2-(2-hydroxy-2-pyridin-4-yl-vinyl)pyridin-3-yl]methanone benzoate, and (2-chlorophenyl)-[2-(2-hydroxy-2-pyridin-4-yl-vinyl)pyridin-3-yl]methanone toluate, which are useful intermediates for the preparation of the compound of Formula I: (I) The present invention further relates to novel processes for preparing a crystalline compound, which is {2-[1-(3,5-bis-trifluoromethyl-benzyl)-5-pyridin-4-yl-1H-[1,2,3]triazol-4-yl]-pyridin-3-yl}-(2-chlorophenyl)-methanone, Form IV.

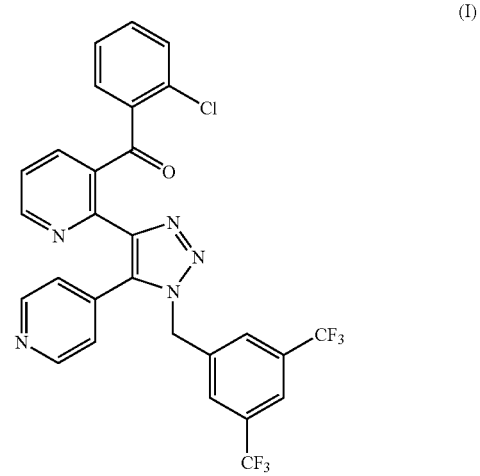

(I)

2 Claims, No Drawings

INTERMEDIATE AND PROCESS USEFUL IN THE PREPARATION OF {2-[1-(3,5-BIS-TRIFLUOROMETHYL-BENZYL)-5-PYRIDIN-4-YL-1H-[1,2,3]TRIAZOL-4-YL]-PYRIDIN-3-YL}-(2-CHLOROPHENYL)-METHANONE

The present invention relates to novel intermediates and a novel process for the preparation of antagonists of the NK1 subtype of tachykinin receptor. Specifically, the present invention provides novel intermediates and a novel process for the preparation of {2-[1-(3,5-bis-trifluoromethyl-benzyl)-5-pyridin-4-yl-1H-[1,2,3]triazol-4-yl]-pyridin-3-yl}-(2-chlorophenyl)-methanone, Form IV.

BACKGROUND OF THE INVENTION

The compound {2-[1-(3,5-bis-trifluoromethyl-benzyl)-5-pyridin-4-yl-1H-[1,2,3]triazol-4-yl]-pyridin-3-yl}-(2-chlorophenyl)-methanone, depicted below as the compound of Formula I, was first described in PCT published application WO2003/091226.

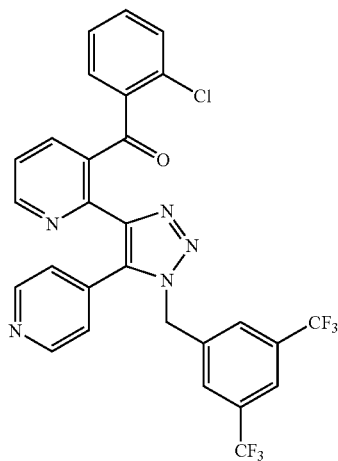 [SMILES: O=C(c1ccccc1Cl)c1cccnc1-c1nnn(Cc2cc(C(F)(F)F)cc(C(F)(F)F)c2)c1-c1ccncc1]

(I)

Because the compound of Formula I is an antagonist of the NK-1 subtype of tachykinin receptor, it is useful for the treatment of disorders associated with an excess of tachykinins. Such disorders include depression, including major depressive disorder; anxiety, including generalized anxiety disorder, panic disorder, obsessive compulsive disorder, and social phobia or social anxiety disorder; schizophrenia and other psychotic disorders, including bipolar disorder; neurodegenerative disorders such as dementia, including senile dementia of the Alzheimer's type or Alzheimer's disease; disorders of bladder function such as bladder detrusor hyperreflexia and incontinence, including urge incontinence; emesis, including chemotherapy-induced nausea and acute or delayed emesis; pain or nociception; disorders associated with blood pressure, such as hypertension; disorders of blood flow caused by vasodilation and vasospastic diseases, such as angina, migraine, and Reynaud's disease; hot flushes; acute and chronic obstructive airway diseases such as adult respiratory distress syndrome, bronchopneumonia, bronchospasm, chronic bronchitis, driver cough, and asthma; inflammatory diseases such as inflammatory bowel disease; gastrointestinal disorders or diseases associated with the neuronal control of viscera such as ulcerative colitis, Crohn's disease, functional dyspepsia, and irritable bowel syndrome (including constipation-predominant, diarrhea-predominant, and mixed irritable bowel syndrome); and cutaneous diseases such as contact dermatitis, a topic dermatitis, urticaria, and other eczematoid dermatitis.

In PCT published application, WO2005/042515, novel crystalline forms of the compound of Formula I, identified as Form IV and Form V, are identified. Also described in WO2005/042515 is a process for preparation of the compound of Formula I, comprising reacting (2-chlorophenyl)-[2-(2-hydroxy-2-pyridin-4-yl-vinyl)pyridin-3-yl]methanone or a phosphate salt thereof with 1-azidomethyl-3,5-bistrifluoromethylbenzene in the presence of a suitable base and a solvent. Use of this procedure results in several shortcomings for synthesis on a commercial scale. For example, use of the solvent DMSO, with (2-chlorophenyl)-[2-(2-hydroxy-2-pyridin-4-yl-vinyl)pyridin-3-yl]methanone phosphate, requires a complex work-up that has a propensity to emulsify. This process also requires extraction with $CH_2Cl_2$, the use of which is discouraged due to its potential as an occupational carcinogen, as well as the use of $MgSO_4$ and acid-washed carbon, which can generate large volumes of waste on a commercial scale. Conducting the reaction with (2-chlorophenyl)-[2-(2-hydroxy-2-pyridin-4-yl-vinyl)pyridin-3-yl]methanone in isopropyl alcohol, as also described in WO2005/042515, is also undesirable due to the need to incorporate a free base step. Furthermore, variable levels of residual 1-azidomethyl-3,5-bistrifluoromethylbenzene, a known mutagen, are obtained from use of the procedures described in WO2005/042515.

An improved process for preparing the compound of Formula I would control the level of 1-azidomethyl-3,5-bistrifluoromethylbenzene impurity, and improve the yield. We have discovered that use of the novel salt, (2-chlorophenyl)-[2-(2-hydroxy-2-pyridin-4-yl-vinyl)pyridin-3-yl]methanone benzoate, as well as use of tert-butanol as the reaction solvent, improves reaction times and final yield, and decreases impurities in the final product. In addition, a novel process for the preparation of (2-chlorophenyl)-[2-(2-hydroxy-2-pyridin-4-yl-vinyl)pyridin-3-yl]methanone benzoate, in which a preformed enolate of 4-acetyl pyridine is added to (2-phenylsulfonyl-pyridine-3-yl)-(2-chlorophenyl)methanone, results in an overall improved yield and improved purity, and is useful on a commercial scale.

SUMMARY OF THE INVENTION

The present invention relates to novel compounds, (2-chlorophenyl)-[2-(2-hydroxy-2-pyridin-4-yl-vinyl)pyridin-3-yl]methanone benzoate, and (2-chlorophenyl)-[2-(2-hydroxy-2-pyridin-4-yl-vinyl)pyridin-3-yl]methanone toluate, which are useful intermediates for the preparation of the compound of Formula I.

The present invention further relates to a process for preparing a crystalline compound, which is {2-[1-(3,5-bis-trifluoromethyl-benzyl)-5-pyridin-4-yl-1H-[1,2,3]triazol-4-yl]-pyridin-3-yl}-(2-chlorophenyl)-methanone, Form IV, comprising: crystallizing the product from a solvent mixture of isopropyl acetate and heptanes.

The present invention further relates to a process for preparing a compound of Formula I comprising reacting a salt of (2-chlorophenyl)-[2-(2-hydroxy-2-pyridin-4-yl-vinyl)pyridin-3-yl]methanone with 1-azidomethyl-3,5-bistrifluoromethylbenzene in the presence of tert-butanol.

DETAILED DESCRIPTION OF THE INVENTION

The terms and abbreviations used in the preparations and examples have their normal meanings unless otherwise designated. Other abbreviations include the following: "h" refers to hour or hours; "HPLC" refers to high performance liquid chromatography; "HRMS" refers to high resolution mass spectrometry; "i-PrOAc" refers to isopropyl acetate; "KOtBu" refers to potassium tert-butoxide; "min" refers to minute or minutes; "MS" refers to mass spectrometry; "NMR" refers to nuclear magnetic resonance spectroscopy; "ppm" refers to parts per million; "RT" refers to room temperature; "TLC" refers to thin layer chromatography; "DMF" refers to N,N-dimethylformamide; "DMSO" refers to dimethylsulfoxide; "MeOH" refers to methanol; "THF" refers to tetrahydrofuran.

As used herein, the term "heptanes" refers to a solution of monovalent, saturated aliphatic chains of 7 carbon atoms. The solution may contain straight chains (n-heptane), or a combination of straight and branched heptanes.

One of ordinary skill in the art will recognize that an alternate name for the compound of Formula I is: Methanone, [2-[1-[[3,5-bis(trifluoromethyl)phenyl]methyl]-5-(4-pyridinyl)-1H-1,2,3-triazol-4-yl]-3-pyridinyl](2-chlorophenyl)-.

The following examples further illustrate the improved process for preparing the compound, {2-[1-(3,5-bistrifluoromethylbenzyl)-5-pyridin-4-yl-1H-[1,2,3]triazol-4-yl]-pyridin-3-yl}-(2-methanone, Form IV.

EXAMPLES

Example 1

{2-[1-(3,5-bistrifluoromethylbenzyl)-5-pyridin-4-yl-1H-[1,2,3]triazol-4-yl]-pyridin-3-yl}-(2-chlorophenyl)-methanone (Form IV)

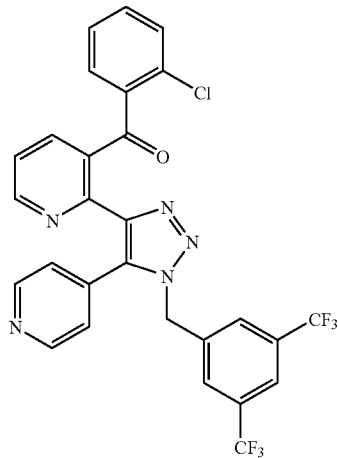

Suspend (2-chlorophenyl)-[2-(2-hydroxy-2-pyridin-4-yl-vinyl)pyridin-3-yl]methanone benzoate (204.7 g; 1.04 equiv; 445 mmoles) in t-butanol (614 mL) and treat the slurry with potassium carbonate (124.2 g; 898.6 mmoles). Heat to 70° C. with mechanical stirring for 1 hour. Add 1-azidomethyl-3,5-bistrifluoromethylbenzene (115.6 g; 1.00 equiv; 429.4 mmoles) in a single portion, then heat the mixture to reflux. A circulating bath is used to maintain a condenser temperature of 30° C. After 18 hours at reflux, HPLC reveals that the reaction is complete (<2% 1-azidomethyl-3,5-bistrifluoromethylbenzene remaining). The mixture is cooled to 70° C., isopropanol (818 mL) is added, then the mixture is stirred at 70° C. for 1 hour. The mixture is filtered, and the waste filter cake is rinsed with isopropanol (409 mL). The combined filtrate and washes are transferred to a reactor, and the mechanically stirred contents are heated to 70° C. To the dark purple solution, water (1.84 L) is added slowly over 35 minutes. The solution is cooled to 60° C., then stirred for 1 hour, during which time a thin precipitate forms. The mixture is slowly cooled to RT, then the solid is filtered, washed with 1:1 isopropanol/water (614 mL), subsequently washed with isopropanol (410 mL), then dried in vacuo at 45° C. to produce 200.3 g of crude {2-[1-(3,5-bistrifluoromethylbenzyl)-5-pyridin-4-yl-1H-[1,2,3]triazol-4-yl]-pyridin-3-yl}-(2-chlorophenyl)-methanone as a white solid. Crude {2-[1-(3,5-bistrifluoromethylbenzyl)-5-pyridin-4-yl-1H-[1,2,3]triazol-4-yl]-pyridin-3-yl}-(2-chlorophenyl)-methanone (200.3 g) and isopropyl acetate (600 mL) are charged to a 5 L 3-neck jacketed flask, then the contents heated to 75° C. After dissolution is achieved, the vessel contents are cooled to 55° C., then the solution polish filtered through a 5 micron filter, and the filter rinsed with a volume of isopropyl acetate (200 mL). After the polish filtration operation is complete, the filtrates are combined, and the vessel contents are adjusted to 50° C. After stirring for at least 15 minutes at 50° C., 0.21 grams of {2-[1-(3,5-bistrifluoromethylbenzyl)-5-pyridin-4-yl-1H-[1,2,3]triazol-4-yl]-pyridin-3-yl}-(2-chlorophenyl)-methanone Form IV seed (d90=40 microns) is added, and the mixture stirred at 50° C. for at least 2 h. Heptanes (1.90 L) are then added over at least 2 h. After the heptanes addition is completed, the slurry is stirred for an hour at 50° C., cooled to 23° C. at a rate less then 20° C. per hour, then aged at 23° C. for an hour prior to isolation. The mixture is then filtered in portions through the bottom outlet valve in the reactor into a 600 mL filter. The resulting wetcake is washed portionwise with a solution containing heptanes (420 mL) and isopropyl acetate (180 mL), which is passed directly through the 5 L crystallization vessel. The wetcake is blown dry for 5 minutes with nitrogen, then transferred to a 500 mL plastic bottle. The product is dried at 50° C. for 4 h. to produce 190.3 g of pure {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV in 75.0% yield with 100% purity, as determined by HPLC analysis. Particle size is reduced via pin or jet mill. $^1$H NMR (400 MHz, CDCl$_3$): 5.46 (s, 2H); 7.19 (m, 5H); 7.36 (dd, 1H, J=4.9, 7.8); 7.45 (s, 2H); 7.59 (m, 1H); 7.83 (s, 1H); 7.93 (dd, 1H, J=1.5, 7.8), 8.56 (dd, 1H, J=1.5, 4.9); 8.70 (d, 2H, J=5.9).

Preparation 1-A (2-chlorophenyl)-[2-(2-hydroxy-2-pyridin-4-yl-vinyl)pyridin-3-yl]methanone benzoate Charge powdered KOtBu (221.1 g, 1.93 moles, 1.40 eq.) to Reactor A, then charge DMSO (2 L) at 25° C. over 10 min. The KOtBu/DMSO solution is stirred for 30 min at 23° C., then a solution of 4-acetyl pyridine (92 mL, 2.07 moles, 1.50 eq) in DMSO (250 mL) is prepared in reactor B. The contents of reactor B are added to Reactor A over 10 minutes, then the Reactor A enolate solution is stirred at 23° C. for 1 h. In a separate 12-L flask (Reactor C), solid LiOH (84.26 g, 3.45 moles, 2.0 eq) is poured into a mixture of (2-phenylsulfonyl-pyridin-3-yl)-(2-chlorophenyl)methanone (500.0 g, 1.34 moles, 1.0 eq) and DMSO (2 L), with stirring, at 23° C. The enolate solution in reactor A is then added to Reactor C over a period of at least 15 minutes, and the red suspension warmed to 40° C. The reaction is stirred for 3 h, after which time HPLC analysis reveals less than 2% (2-phenylsulfonyl-pyridin-3-yl)-(2-chlorophenyl)methanone. Toluene (2.5 L) is charged, and the reactor temperature cooled to 30° C. The mixture is quenched by addition of glacial acetic acid (316 mL, 5.52 moles, 4.0 eq), followed by 10% NaCl (2.5 L). The biphasic mixture is transferred to a 22-L bottom-outlet Morton flask, and the aqueous layer is removed. The aqueous layer is then extracted with toluene (750 mL). The combined organic layers are washed with 10% NaCl (750 mL), then concentrated to 4 volumes and transferred to a 12-L Morton flask and rinsed with isopropyl acetate (4 vol, 2 L). The opaque amber solution is warmed to 75 degrees to 75° C. over be run reproducibly from 0.4 to 2 kg scale to give yields of 77-83%, with >99% purity. In addition, the reaction can be held overnight at 40° C. with minimal degradation, whereas holding the reaction for 1 h past completion at 60-70° C. results in substantial aromatized impurity. The reaction may also be performed using sodium tert-amylate as the base, in combination with an aprotic solvent, such as DMSO or DMF.

The title compound exists as a mixture of tautomers and geometric isomers. It is understood that each of these forms is encompassed within the scope of the invention.

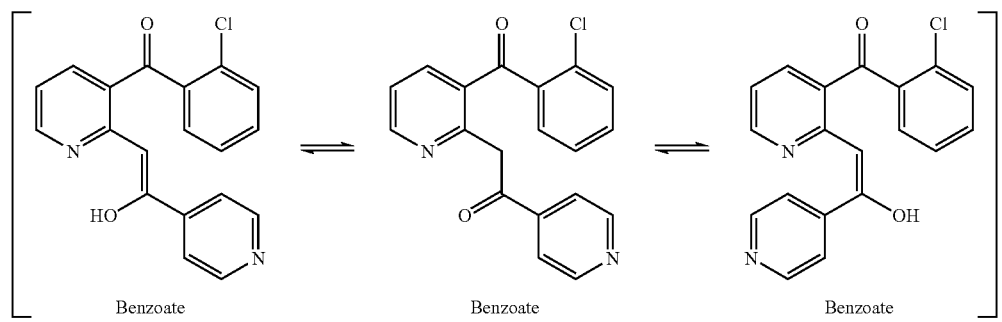

Benzoate        Benzoate        Benzoate 40 min. Benzoic acid (171.1 g, 1.34 moles, 1.0 eq) is dissolved in hot isopropyl acetate (1.5 L), and charged to the crude free base solution over at least 30 min. The crude solution containing benzoate salt is stirred for 0.5 h at 75° C. then cooled to 23° C. When solids are first observed, the cooling is stopped and the mixture is aged for an hour at the temperature at which crystals are first observed. Alternatively, if seed crystal is available, the mixture may be seeded with (2-chlorophenyl)-[2-(2-hydroxy-2-pyridin-4-yl-vinyl) pyridin-3-yl]methanone benzoate (2.25 g) at 75° C., followed by stirring for 0.5 h at 75° C., then cooling to 23° C. over at least 1.5 h. The mixture is then cooled to <5° C., then filtered through paper on a 24 cm single-plate filter. The filter cake is then rinsed with cold i-PrOAc (750 mL) to produce granular crystals of bright orange-red color. The wet solid is dried at 55° C. to produce 527.3 g (83% yield) with 99.9% purity. (2-chlorophenyl)-[2-(2-hydroxy-2-pyridin-4-yl-vinyl)pyridin-3-yl]methanone benzoate. Anal. Calcd. for $C_{26}H_{19}N_2ClO_4$: C, 68.05; H, 4.17; N, 7.13. Found: C, 67.89; H, 4.15; N 6.05. HRMS: calcd for $C_{19}H_{13}ClN_2O_2$, 336.0666. found 336.0673.

The synthesis of (2-chlorophenyl)-[2-(2-hydroxy-2-pyridin-4-yl-vinyl)pyridin-3-yl]methanone benzoate proceeds optimally when the potassium enolate of 4-acetyl pyridine is pre-formed using KOtBu in DMSO. Pre-formation of the enolate allows the SNAR (nucleophilic aromatic substitution) reaction to be performed between room temperature and 40° C., which minimizes the amount of degradation. Under these conditions, the SNAR is highly regioselective, resulting in a ratio of approximately 95:5 preferential C-acylation. In all cases, less polar solvents such as THF or toluene, or co-solvents of these solvents mixed with DMSO, results in a substantial increase of acylation at the oxygen in the SNAR, and leads to a lower yield of product. This is a substantial improvement over the procedures described in WO2005/042515 for synthesis of the free base or the phosphate salt, in which the SNAR is performed at 60-70° C., resulting in a substantial increase in chemical impurity. Using the conditions described in WO2005/042515, when scaled to 2 kg, results in maximum yields of 55%, with sub-optimal potency. In comparison, the improved conditions described herein can Preparation 1-B (2-chlorophenyl)-[2-(2-hydroxy-2-pyridin-4-yl-vinyl)pyridin-3-yl]methanone toluate The procedure described in Preparation 1-A is followed, with the following exception. Solid toluic acid (1.0 eq) is added to the crude free base solution at 55° C., then the solution cooled to 45° C. The solution is stirred for one hour at 45° C., then slowly cooled to 23° C. When solids are first observed, the cooling is stopped and the mixture is aged for an hour at the temperature at which crystals are first observed. Alternatively, if seed crystal is available, the mixture may be seeded, aged for 3 h at 45° C., then cooled to 0° C. over 4 h. The isolation slurry is filtered, and the wetcake washed with MeOH (3 volumes). The wetcake is dried at 50° C. to provide 14.0 g (76.4%) of (2-chlorophenyl)-[2-(2-hydroxy-2-pyridin-4-yl-vinyl)pyridin-3-yl]methanone toluate as a light red powder.

As with the benzoate salt, the toluate salt can also exist as a mixture of tautomers and geometric isomers, each of which is encompassed within the scope of the invention. (2-chlorophenyl)-[2-(2-hydroxy-2-pyridin-4-yl-vinyl)pyridin-3-yl] methanone toluate. $^{13}$C NMR (125 MHz, DMSO-d6) δ 194.5, 167.8, 167.4, 155.5, 150.7 (2C), 147.4, 144.0, 143.4, 142.7, 138.6, 133.0, 130.8, 130.7, 130.5, 129.8 (2C), 129.5 (2C), 128.5, 128.0, 127.9, 119.9 (2C), 118.6, 92.6, 21.5.

Preparation 1-C (2-phenylsulfonyl-pyridin-3-yl)-(2-chlorophenyl) methanone

A solution of 1.3 eq of diisopropylamine (based on 2-benzenesulfonyl pyridine) in 5 volumes of THF in a mechanically stirred 3-necked flask is cooled to −70 to −75° C. To this solution is added 1.05 eq of n-butyllithium (1.6M in hexanes) at such a rate as to maintain the temperature below −60° C. The light yellow solution is stirred at −60 to −70° C. for 30 minutes. Once the temperature has cooled back down to −60 to −65° C., 1.0 eq of 2-benzene-sulfonyl pyridine, as a solution in 3 volumes of THF, is added at the fastest rate that will maintain the reaction temperature under −60° C. A yellow suspension forms during the addition that becomes yellow-orange upon longer stirring. This mixture is stirred for 3 hours at −60 to −75° C., and then 1.06 eq of 2-chlorobenzaldehyde, as a solution in 1 volume of THF, is added dropwise at a sufficient rate to keep the temperature under −55° C. The suspension gradually turns orange-red, thins out, and then becomes a clear red solution. The reaction mixture is allowed to stir at −60 to −70° C. for 1 hour, 3N aqueous HCl (7 volumes) is added over 20-30 minutes, and the temperature is allowed to exotherm to 0-10° C. The color largely disappears, leaving a biphasic yellow solution. The solution is warmed to at least 10° C., the layers are separated, and the aqueous layer is back-extracted with 10 volumes of ethyl acetate. The combined organic layers are washed with 10 volumes of saturated sodium bicarbonate solution and concentrated to about 2 volumes. Ethyl acetate (10 volumes) is added, and the solution is once again concentrated to 2 volumes. The thick solution is allowed to stand overnight and is taken to the next step with no purification of the crude alcohol intermediate. The crude alcohol intermediate is transferred to a 3-necked flask with enough ethyl acetate to make the total solution about 10 volumes. The yellow solution is treated with 3.2 volumes of 10% aqueous (w/w) potassium bromide, followed by 0.07 eq of 2,2,6,6-Tetramethylpiperidine-N-oxide (TEMPO). The orange mixture is cooled to 0-5° C. and treated with a solution of 1.25 eq of sodium bicarbonate in 12% w/w sodium hypochlorite (9 volumes) and 5 volumes of water over 30-60 minutes while allowing the temperature to exotherm to a maximum of 20° C. The mixture turns dark brown during the addition, but becomes yellow, and a thick precipitate forms. The biphasic light yellow mixture is allowed to stir at ambient temperature for 1-3 hours, at which time the reaction is generally completed. The biphasic mixture is cooled to 0-5° C. and stirred for 3 hours at that temperature. The solid is filtered off, washed with 4 volumes of cold ethyl acetate, followed by 4 volumes of water, and dried in vacuo at 45° C. to constant weight. Typical yield is 80-83% with a purity of greater than 98%. $^1$H NMR (600 MHz, CDCl$_3$-d) δ ppm 7.38 (td, J=7.52, 1.28 Hz, 1H) 7.47 (dd, J=7.80, 1.30 Hz, 1H) 7.51 (td, J=7.79, 1.60 Hz, 1H) 7.51 (t, J=7.89 Hz, 2H) 7.50-7.54 (m, J=7.75, 4.63 Hz, 1H) 7.60 (t, J=7.43 Hz, 1H) 7.73 (dd, J=7.75, 1.60 Hz, 1H) 7.81 (dd, J=7.79, 1.56 Hz, 1H) 8.00 (dd, J=8.44, 1.10 Hz, 2H) 8.76 (dd, J=4.63, 1.61 Hz, 1H).

Preparation 1-D 1-azidomethyl-3,5-bistrifluoromethyl-benzene

Sodium azide (74.3 g, 1.14 mol) is suspended in water (125 mL), then DMSO (625 mL) is added. After stirring for 30 minutes, a solution consisting of 3,5-Bis(trifluoromethyl) benzyl chloride (255.3 g, 0.97 moles) and DMSO (500 mL) is added over 30 minutes. (The 3,5-Bis(trifluoromethyl)benzyl chloride is heated to 35° C. to liquefy prior to dispensing (MP=30-32° C.)). The benzyl chloride feed vessel is rinsed with DMSO (50 mL) into the sodium azide solution, the mixture is heated to 40° C., and then maintained for an hour at 40° C., then cooled to 23° C.

In Process Analysis:
A drop of the reaction mixture is dissolved in d6-DMSO and the relative intensities of the methylene signals are integrated (NMR verified as a 0.35% limit test for 3,5-Bis(trifluoromethyl)benzyl Chloride).

Work-Up:
After the mixture reaches 23° C., it is diluted with heptanes (1500 mL), then water (1000 mL) is added, and the mixture exotherms to 35° C. against a jacket setpoint of 23° C. The aqueous layer is removed (~2200 mL), then the organic layer (approximately 1700 mL) is washed with water (2×750 mL). The combined aqueous layers (~3700 mL) are analyzed and discarded.

The solvent is then partially removed via vacuum distillation with a jacket set point of 85° C., pot temperature of 60-65° C. and distillate head temperature of 50-55° C. to produce 485 g (94.5% yield) of 51 Wt % solution title compound as a clear liquid. Heptanes can be either further removed by vacuum distillation or wiped film evaporation technology. $^1$H NMR (400 MHz, CDCl$_3$): 4.58 (s, 2H); 7.81 (s, 2H); 7.90 (s, 1H).

Preparation 1-E 2-benzene-sulfonyl pyridine

Charge 2-chloropyridine (75 mL, 790 mmol), thiophenol (90 mL, 852 mmol), and DMF (450 mL) to a 2 L flask. Add K$_2$CO$_3$ (134.6 g, 962 mmol), then heat to 110° C. and stir for 18 hours. Filter the mixture, then rinse the waste cake with DMF (195 mL). The combined crude sulfide solution and rinses are transferred to a 5-L flask, and the waste filter cake is discarded. Glacial acetic acid (57 mL, 995 mmol) is added to the filtrate, then the solution is heated to 40° C., and 13 wt % NaOCl solution (850 mL, 1.7 mol) is added over 2 hours. After the reaction is complete, water (150 mL) is added, then the pH of the mixture adjusted to 9 with 20% (w/v) NaOH solution (250 mL). The resulting slurry is cooled to <5° C., stirred for 1.5 h, then filtered, and the cake washed with water (3×200 mL). The product wetcake is dried in a 55° C. vacuum oven to provide 2-benzene-sulfonyl pyridine (149 g, 676 mmol) in 86% yield: $^1$H NMR (500 MHz, CDCl$_3$) δ 8.66 (d, J=5.5 Hz, 1H), 8.19 (d, J=7.7 Hz, 1H), 8.05 (m, 2H), 7.92 (ddd, J=9.3, 7.7, 1.6 Hz, 1H), 7.60 (m, 1H), 7.54 (m, 2H), 7.44 (m, 1H); IR (KBr) 788, 984, 1124, 1166, 1306, 1424, 1446, 1575, 3085 cm$^{-1}$; MS (TOF) m/z 220.0439 (220.0427 calcd for C$_{11}$H$_{10}$NO$_2$S, MH); Anal. calcd for C$_{11}$H$_9$NO$_2$S: C, 60.26; H, 4.14; N, 6.39; S, 14.62. Found: C, 60.40; H, 4.02; N, 6.40; S, 14.76.

As noted above, use of the improved process of the present invention results in an improved habit of the crystalline Form IV compound of Formula I. The improved habit reduces surface area of the crystal, improves the filtration, and washing, and improves the efficiency of azide mutagen rejection. These improvements are described in greater detail below.

In patent application WO2005/042515, the polish filtration is carried out in 7 volumes (L/kg) of isopropanol near its boiling point (65-83° C.), a process that is difficult and hazardous to execute in commercial manufacturing because of the high risk of crystallization on the filter and/or vessel transfer lines due to supersaturation. In the preferred crystallization solvent, isopropyl acetate, the polish filtration is conducted in four volumes of isopropyl acetate at temperatures from 45 to 55° C. This temperature range is 35 to 45° C. lower than the boiling point of isopropyl acetate, which provides a key safety advantage. Under these conditions, {2-[1-(3,5-bistrifluoromethylbenzyl)-5-pyridin-4-yl-1H-[1,2,3]triazol-4-yl]-pyridin-3-yl}-(2-chlorophenyl)-methanone will remain in solution for days, and there is no danger of crystallization and clogging of filter and transfer lines. Controlled crystallization is conducted by seeding with Form IV crystals at 40-45° C., followed by a ripening period of at least 2 hrs, then addition of 12-15 volumes of an anti-solvent, preferably heptanes, which maximizes process yields.

Larger API crystals with the preferred habit (e.g., prisms and rods, as opposed to needles) provide favorable processing characteristics, including fast filtration, efficient washing and good powder flow properties. Data from four sample filtrations, conducted in the FLT-37 Hastelloy® filter-drier on a 2-3 kg scale, are provided below. The data show an average increase in filtration rate of three- to four-fold (Flux data) for the preferred isopropyl acetate/heptanes system relative to the prior isopropyl alcohol solvent system.

| Isopropyl acetate/heptanes filtration | | | | |
| --- | --- | --- | --- | --- |
| Lot Number | A | B | C | D |
| Flux (L/m$^2$ · h.) | 8,858 | 11,106 | 12,930 | 10,807 |
| Filtration Time (min) | 11 | 7 | 8 | 9 |
| Wetcake thickness (mm) | 130 | 97 | 125 | 100 |

| Isopropyl alcohol filtration | | | | |
| --- | --- | --- | --- | --- |
| Lot Number | A | B | C | D |
| Flux (L/m$^2$ · h.) | 3,424 | 2,133 | 2,712 | 2,002 |
| Filtration Time (min) | 24 | 43 | 31 | 32 |
| Wetcake thickness (mm) | 145 | 140 | 140 | 138 |

A unimodal particle size distribution is optimally achieved with seeding where seed particle size consists of a $d_{90}$<20 microns, seed load=0.1 wt %, seed temperature=50° C., seed age time=2 h, and heptanes feed rate=2 hr. In another preferred embodiment, the seed particle size consists of a $d_{90}$=40 microns, seeding temperature=55° C., seed load=0.1-2%.

In the preferred embodiment, the final product is milled to a target particle size for optimal use in the drug product. The preferred methods of milling include, but are not limited to, pin mill, turbo rotor, jet mill and slurry mill. Jet mill technology produces final product with d90 of approximately 10 microns.

The preferred crystallization system using isopropyl acetate/heptanes is found to be optimal to remove methanone positional isomer impurities and azide. Spiking studies have revealed that these impurities are completely purged from the final product under the preferred processing conditions described herein.

The free base of (2-chlorophenyl)-[2-(2-hydroxy-2-pyridin-4-yl-vinyl)pyridin-3-yl]methanone does not crystallize directly from the crude reaction mixture, and conversion to a salt form for purification is essential. The benzoate and toluate salts of (2-chlorophenyl)-[2-(2-hydroxy-2-pyridin-4-yl-vinyl)pyridin-3-yl]methanone, described herein, are readily prepared from the crude free base, as described above. Both the benzoate and toluate salts have an improved morphology relative to the phosphate salt. Both the benzoate and toluate salts exist in a large plated morphology as compared to the needle-like morphology of the phosphate salt. This difference in morphology results in a substantially improved isolation rate for the benzoate and toluate salts. The improved morphology translates to a higher bulk density of isolated solid (0.4-0.5 g/L) for the benzoate or toluate salts, as compared to the phosphate salt (0.1-0.2 g/L). This results in increased drier capacity. In addition, both the benzoate and toluate salts are free flowing solids, whereas the phosphate salt appears to contain considerable static. Generally, the benzoate salt is the most preferred embodiment.

What is claimed is:

1. A process for preparing a compound that is {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV, comprising: crystallizing the product from a solvent mixture of isopropyl acetate and heptanes,
wherein the {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV is characterized by at least one of the following:
a) a solid-state $^{13}$C nuclear magnetic resonance spectrum comprising peaks at the following chemical shifts: 52.3±0.2 and 195.4±0.2 ppm;
b) an X-ray powder diffraction pattern comprising at least two peaks wherein one peak is 12.1±0.1° and the second peak is selected from the group consisting of 8.3±0.1°, 14.3±0.1°, 16.6±0.1°, 16.9±0.1°, and 18.5±0.1° in 2θ; or
c) an X-ray powder diffraction pattern comprising at least the following peaks: 8.3±0.1°, 12.1±0.1°, 16.6±0.1°, 16.9±0.1°, and 18.5±0.1° in 2θ.

2. The process of claim 1, wherein the {2-[1-(3,5-bistrifluoromethylbenzyl)-5-pyridin-4-yl-1H-[1,2,3]triazol-4-yl]-pyridin-3-yl}-(2-chlorophenyl)-methanone, Form IV is characterized by an X-ray powder diffraction pattern comprising at least the following peaks: 6.8±0.1°, 7.7±0.1°, 8.3±0.1°, 11.2±0.1°, 12.1±0.1°, 12.7±0.1°, 13.5±0.1°, 14.3±0.1°, 14.9±0.1°, 16.2±0.1°, 16.6±0.1°, 16.9±0.1°, 17.4±0.1°, 18.2±0.1°, 18.5±0.1°, 18.9±0.1°, 19.3±0.1°, 19.8±0.1°, 20.3±0.1°, 20.7±0.1°, 21.1±0.1°, 21.4±0.1°, 21.7±0.1°, 21.9±0.1°, 22.1±0.1°, 22.5±0.1°, 22.8±0.1°, 23.4±0.1°, 24.0±0.1°, 24.3±0.1°, 24.9±0.1°, 25.6±0.1°, 25.9±0.1°, 26.4±0.1°, 26.9±0.1°, 27.3±0.1°, 28.1±0.1°, 28.5±0.1°, 29.0±0.1°, 29.3±0.1°, 29.9±0.1°, 30.2±0.1°, 31.3±0.1°, 31.5±0.1°, 32.6±0.1°, 33.3±0.1°, 35.4±0.1°, 36.1±0.1°, 36.4±0.1°, and 36.8±0.1° in 2θ.

* * * * *